(12) United States Patent
Reinhardt et al.

(10) Patent No.: US 12,740,707 B2
(45) Date of Patent: Sep. 22, 2026

(54) CALIBRATION UNIT FOR A MACROSCOPIC MEDICAL IMAGING DEVICE, MACROSCOPIC MEDICAL IMAGING CALIBRATION SYSTEM AND USE OF A CALIBRATION UNIT

(71) Applicant: Ivoclar Vivadent AG, Schaan (LI)

(72) Inventors: Jonas Reinhardt, Igis (CH); Raimund Tichy, Feldkirch (AT); Alexander Grosse-Honebrink, Arbon (CH); Elbert De Josselin De Jong, Bussum (NE); Erik Van Den Heuvel, Bussum (NE)

(73) Assignee: Ivoclar Vivadent AG, Schaan (LI)

( * ) Notice: Subject to any disclaimer, the term of this patent is extended or adjusted under 35 U.S.C. 154(b) by 383 days.

(21) Appl. No.: 18/355,156

(22) Filed: Jul. 19, 2023

(65) Prior Publication Data

US 2024/0023810 A1 Jan. 25, 2024

(30) Foreign Application Priority Data

Jul. 20, 2022 (EP) .................................... 22186088

(51) Int. Cl.
*A61B 5/00* (2006.01)
*A61B 5/145* (2006.01)
(Continued)

(52) U.S. Cl.
CPC ............ *A61B 5/0071* (2013.01); *A61B 5/004* (2013.01); *A61B 5/0088* (2013.01); *A61B 5/145* (2013.01);
(Continued)

(58) Field of Classification Search
CPC ... A61B 5/0071; A61B 5/1455; A61B 5/0062; A61B 5/004; A61B 5/0088;
(Continued)

(56) References Cited

U.S. PATENT DOCUMENTS 4,184,175 A 1/1980 Mullane, Jr.
6,352,862 B1 * 3/2002 Davis ............... G01N 33/54388 436/814
(Continued)

FOREIGN PATENT DOCUMENTS

CA 3009411 A1 * 1/2010 ............... A61C 5/90
CA 3145141 A1 * 12/2020 ............. G01N 21/77
(Continued)

*Primary Examiner* — Sean P Dougherty
(74) *Attorney, Agent, or Firm* — Ann M. Knab; Thad McMurray

(57) ABSTRACT

A calibration unit for the calibration of a macroscopic medical imaging device. The calibration unit is especially suitable for the calibration of a macroscopic dental imaging device. The calibration unit comprises a main body having a front surface being configured for being optically oriented towards the imaging device. Moreover, a fluorescent material of a first type is arranged in a first sector of the main body. Furthermore, a fluorescent material of a second type is arranged in a second sector of the main body. Alternatively or additionally to the fluorescent material of the second type, an opaque, non-fluorescent material is arranged in a third sector of the main body. Additionally, a macroscopic medical imaging calibration system, especially a macroscopic dental imaging calibration system is presented. Moreover, a use of the calibration unit as described above for the calibration of a macroscopic medical imaging device, especially for the calibration of a macroscopic dental imaging device, is explained.

17 Claims, 7 Drawing Sheets

(51) Int. Cl.

| | |
|---|---|
| ***A61B 5/1455*** | (2006.01) |
| ***A61C 19/04*** | (2006.01) |
| ***A61C 19/06*** | (2006.01) |
| ***G01M 11/00*** | (2006.01) |
| ***G01N 21/64*** | (2006.01) |
| ***G01N 21/65*** | (2006.01) |

(52) U.S. Cl.

CPC ..... *A61B 5/1455* (2013.01); *A61B 2560/0238* (2013.01); *A61C 19/04* (2013.01); *A61C 19/06* (2013.01); *G01M 11/00* (2013.01); *G01N 21/64* (2013.01); *G01N 21/65* (2013.01)

(58) Field of Classification Search

CPC .............. A61B 2560/0238; A61B 1/24; A61B 1/00057; A61B 2560/0223; G01M 11/00; G01N 21/64; G01N 21/65; A61C 19/04

See application file for complete search history.

(56) References Cited

U.S. PATENT DOCUMENTS

| | | | | |
|---|---|---|---|---|
| 10,743,749 | B2 * | 8/2020 | Yamada | A61B 5/0075 |
| 2005/0255423 | A1 | 11/2005 | Hack et al. | |
| 2011/0117025 | A1 * | 5/2011 | Dacosta | A61B 5/742<br>435/5 |
| 2013/0141558 | A1 | 6/2013 | Jeon et al. | |

FOREIGN PATENT DOCUMENTS

| | | | | |
|---|---|---|---|---|
| DE | 10043749 | A1 | 3/2002 | |
| JP | 2014090780 | A | 5/2014 | |
| WO | WO-2014017065 | A1 * | 1/2014 | A61B 1/00057 |

* cited by examiner 28
58
62
56
40
42
58
64
60
VII
46
54
44
54
52
48

28
52
58
60
40
62
42
58
56
64

28
42
56
58
62
54
40
64
60
46
52
54
48
44
54
58
50
54

CALIBRATION UNIT FOR A MACROSCOPIC MEDICAL IMAGING DEVICE, MACROSCOPIC MEDICAL IMAGING CALIBRATION SYSTEM AND USE OF A CALIBRATION UNIT

CROSS-REFERENCE TO RELATED APPLICATIONS

This application claims priority to European Patent Application No. 22186088.5 filed on Jul. 20, 2022, the disclosure of which is incorporated herein by reference in its entirety.

TECHNICAL FIELD

The invention is directed to a calibration unit for the calibration of a macroscopic medical imaging device, especially for the calibration of a macroscopic dental imaging device.

The invention additionally relates to a macroscopic medical imaging calibration system, especially a macroscopic dental imaging calibration system. The invention is further directed to a use of a calibration unit as described above.

BACKGROUND

The designation of the above-mentioned imaging devices as macroscopic is to be understood as a differentiation over microscopic imaging devices or simply microscopes. Thus, the present invention is not about microscopic imaging devices.

Macroscopic medical imaging devices, especially macroscopic dental imaging devices, are known. Such devices are used for capturing images of a human body or parts thereof. The content of the images may be analyzed and, in doing so, certain diseases or pathogens may be recognized in the images. In a case in which the medical imaging device is a dental imaging device, it is specifically adapted to capture images of the oral cavity or parts thereof of a human being.

In the context of macroscopic dental imaging devices, intra-oral cameras, extra-oral cameras and so-called intra-oral scanners may be used as imaging devices for capturing images of the oral cavity or parts thereof.

Such imaging devices may be used for producing white light images of the intra-oral environment.

Moreover, it is known that both sound teeth as well as certain dental pathogens are fluorescent. In this context, fluorescence is to be understood as the ability of a material to emit light, or more generally electromagnetic radiation, when being excited by light, or more generally electromagnetic radiation. Such a material at least partially absorbs the excitation light or excitation radiation. In most cases, the emitted light or radiation has a longer wavelength than the absorbed light or radiation. Based on this effect, also fluorescence images may be taken of the oral cavity or parts thereof.

Both types of images are used in support of diagnoses. U.S. Pat. No. 4,184,175 and US application nos. 20050255423 and 20130141558 are directed to devices for diagnostic and/or calibration applications and are hereby incorporated by reference.

SUMMARY

The objective of the present invention is to further improve macroscopic dental imaging devices such that especially fluorescence images of enhanced quality may be provided.

The problem is solved by a calibration unit for the calibration of a macroscopic medical imaging device, especially for the calibration of a macroscopic dental imaging device. The calibration unit comprises a main body having a front surface being configured for being optically oriented towards the imaging device. A fluorescent material of a first type is arranged in a first sector of the main body. Moreover, a fluorescent material of a second type is arranged in a second sector of the main body. The first sector and the second sector are separate from one another and the fluorescent material of the first type is different from the fluorescent material of the second type. Additionally or alternatively to the second sector and the fluorescent material of the second type, an opaque, non-fluorescent material is arranged in a third sector of the main body. The third sector is separate from each of the first sector and the second sector. It is noted that the terms first, second and third are used for the ease of explanation only. These terms do not imply a certain number of materials or sectors. A sector is to be understood as a volumetric portion of the main body. The sector can have any shape. Using such a calibration unit, the macroscopic medical imaging device, especially the macroscopic dental imaging device, may be calibrated to a ground truth which is represented by the calibration unit. Thus, if two or more macroscopic medical imaging devices or two or more macroscopic dental imaging devices are calibrated using the same or similar calibration units, the comparability of the images being produced by these imaging devices is enhanced. This means that images having been captured by one imaging device may be compared with high reliability to images having been captured by another imaging device. Moreover, since the macroscopic medical imaging device or the macroscopic dental imaging device may be calibrated more than once over time, the use of a calibration unit also enhances the comparability of images which have been captured at different points in time. In other words, using a calibration unit has the effect that captured images are comparable over time and over devices. Moreover, images which have been captured by a calibrated imaging device may be analyzed in a quantitative manner. In the case of a macroscopic dental imaging device, dental pathogens which are represented in the images may be quantified. This enhances a diagnosis being based on the image. Following the above explanations, also the quantitative analyses are made comparable over time and over devices by use of the calibration unit. Altogether, the quality of images being captured by a macroscopic medical imaging device or a macroscopic dental imaging device is improved.

In this context, the fluorescent material of a first type, the fluorescent material of a second type and/or the opaque, non-fluorescent material may be chosen such that these materials mimic the optical properties of either a sound portion of the human body or a body portion being unsound due to a widespread disease or a widespread pathogen.

In the context of a macroscopic dental imaging device, the fluorescent material of the first type may mimic the fluorescent properties of sound teeth. Sound teeth emit light in the green spectrum when being excited using light in the UV or blue spectrum, e.g. light having a wavelength of 200 nm to 500 nm.

The fluorescent material of the second type may mimic the fluorescent properties of a first dental pathogen and the opaque, non-fluorescent material may mimic the optical properties of a second dental pathogen. In an example, the fluorescent material of the second type may mimic the fluorescent properties of a carious lesion. As compared to sound teeth, the fluorescence emission of teeth with a carious lesion shows a shift towards the red spectrum when being excited using light in the UV, blue or green spectrum. An advanced carious lesion shows a bright red fluorescence resulting from the presence of porphyrins which are produced by cariogenic bacteria. The same is true for dental calculus and dental plaque.

The opaque, non-fluorescent material may mimic the optical properties of a so-called white-spot lesion. As compared to sound teeth, the emission of teeth with a white-spot lesion show a reduction of green fluorescence due to light scattering in the affected enamel.

In all of the above examples, the calibration unit allows for a very precise calibration of a macroscopic medical imaging device. This is due to the fact that the calibration unit is designed such that it offers fluorescent properties that correspond to or are close to the real use case. This means that wavelengths or spectra to which the imaging device is calibrated are the same or are close to the wavelengths or spectra that need to be captured during use of the imaging device.

According to an embodiment, a translucent material is arranged in a fourth sector of the main body. The fourth sector is separate from each of the first sector, the second sector, and the third sector. Preferably, the translucent material is also transparent. In this case, the translucent material can be used to mimic enamel which is also transparent. Consequently, in a dental application, pathogens or diseases occurring below the surface of a tooth, i.e. below the enamel, may be mimicked by the calibration unit. Thus, using the calibration unit, an imaging device can be calibrated such that it is able to detect below-surface pathogens or diseases with high reliability.

In an example, at least one of the first sector, the second sector and the third sector is at least partially surrounded by the fourth sector. In this context, the translucent or transparent material of the fourth sector may also be used for holding together some or all of the remaining sectors, i.e. the first sector, the second sector, the third sector or a sub-set thereof. Moreover, this configuration leads to a highly compact calibration unit.

According to a variant, the main body comprises at least one supplementary sector, wherein the fluorescent material of the first type, the fluorescent material of the second type or the opaque, non-fluorescent material is arranged in the supplementary sector. In other words, the fluorescent material of the first type, the fluorescent material of the second type or the opaque, non-fluorescent material may be arranged in an additional sector. It is understood that the supplementary sector is separate from all other sectors. Consequently, when performing a calibration using the calibration unit, a calibration with respect to the material of the supplementary sector can be based on two sectors which are arranged in different locations. Consequently, the uniformity of the calibration over a field of view of the imaging device can be enhanced.

It is noted that the present invention is not limited to a fluorescent material of the first type and a fluorescent material of the second type. Depending on the application, it is also possible to use additional fluorescent materials of further types having optical properties which are suitable for mimicking optical effects of the human body that are used for imaging.

At least one of the first sector, the second sector, the third sector, the fourth sector, and the supplementary sector may be formed as a layer of the main body. The layer may extend parallel to the front surface. Such a layer may be manufactured in an efficient manner. Moreover, providing one of the sectors in the form of a layer renders the calibration unit compact.

The layer may be arranged at a distance from the front surface. Thus, in a dental application, pathogens or diseases occurring below the surface of a tooth may be mimicked by the material of the sector being formed as such a layer. The same is true for a medical application in general. Using the calibration unit, an imaging device can be calibrated such that it is able to detect below-surface pathogens or diseases with high reliability. Preferably, a space being formed between the front surface and such a layer may be filled with translucent or transparent material, e.g. the translucent or transparent material of the fourth sector.

It is also possible that at least one of the first sector, the second sector, the third sector, and the supplementary sector is cylinder-shaped, cone-shaped, polyhedron-shaped or ellipsoid-shaped. Using such a shape facilitates embedding the at least one of the first sector, the second sector, the third sector, and the supplementary sector in the fourth sector, thereby forming a compact calibration unit which at the same time offers a comparatively high variety of calibration targets.

In this context, the front surface may coincide with an end surface of at least one of the first sector, the second sector, the third sector, and the supplementary sector. This means that from the perspective of an imaging device being calibrated using the calibration unit, the end surface of at least one of the first sector, the second sector, the third sector, and the supplementary sector is not covered. Such a sector may be used for mimicking a pathogen or a disease which usually occurs on a surface of a part of the human body, especially on a surface of a tooth. Thereby, the calibration reliability is enhanced.

According to a variant, a portion of the front surface which coincides with an end surface of at least one of the first sector, the second sector, the third sector, and the supplementary sector is locally curved. The portion of the front surface may be convexly curved, i.e. may bulge towards an exterior of the calibration unit. Alternatively, the portion of the front surface may be concavely curved, i.e. may form a depression in the calibration unit. The portion of the front surface where the front surface coincides with an end surface of at least one of the first sector, the second sector, the third sector, and the supplementary sector may alternatively comprise a plurality of curved sections, e.g. a plurality of sections bulging towards an exterior, or a plurality of depressions. It is also possible that some sections bulge towards the exterior and some form depressions. Since human teeth also have humps and depressions, the calibration reliability is further enhanced.

In an alternative, an end face being oriented towards the front surface of at least one of the first sector, the second sector, the third sector, and the supplementary sector may be arranged at a distance from the front surface. Thus, in a dental application, pathogens or diseases occurring below the surface of a tooth may be mimicked by the material of the sector having such an end face. The same applies for a medical use in general. Using the calibration unit, an imaging device can be calibrated such that it is able to detect below-surface pathogens or diseases with high reliability. Preferably, a space being formed between the front surface and such an end face may be filled with translucent or transparent material, e.g. the translucent or transparent material of the fourth sector.

In a preferred example, the first sector is formed as a layer being arranged at a distance from the front surface and covering a full width of the main body. In this example, also the fourth sector may be formed as a layer, wherein the fourth sector fully fills the space between the front surface and the first sector. The second sector may be fully or partially embedded in the fourth sector. Alternatively or additionally, the third sector may be fully or partially embedded in the fourth sector. Further alternatively or additionally, at least one supplementary sector may be fully or partially embedded in the fourth sector. Such a calibration unit offers a plurality of calibration target and at the same time is compact and easy to manufacture.

In an example, the fluorescent material of the first type is a green fluorescent material. As has already been mentioned, also sound teeth comprise a green fluorescent material. Thus, a green fluorescent material is particularly suitable for mimicking the fluorescent properties of sound teeth. An imaging device being calibrated by a calibration unit according to the invention is, thus, able to detect sound teeth with high reliability.

In another example, the fluorescent material of the second type is a red fluorescent material. As has already been mentioned before, also a carious lesion comprises a red fluorescent material. Thus, a red fluorescent material is particularly suitable for mimicking the fluorescent properties of a carious lesion. An imaging device being calibrated by a calibration unit according to the invention is, thus, able to detect a carious lesion with high reliability.

According to an embodiment, at least one of the first sector, the second sector, the third sector, the fourth sector and the supplementary sector comprises a dental restoration material. Dental restoration materials usually mimic the properties of natural dental material. Thus, the materials of the calibration unit are similar to the materials to be inspected. This leads to enhanced image quality.

The dental restoration material may be a light curing material or a photopolymerizable material. Such materials are cured by blue light or UV light. Examples of such materials are Tetric™ Prime, Tetric™ EvoFlow™, Tetric™ Powerfill, Tetric™ Powerflow, and Tetric™ EvoCeram™. All these materials are commercially available products of Ivoclar Vivadent AG, Liechtenstein.

The dental restoration material may as well be an inorganic material such as metal, ceramic, glass and glass-ceramic. Examples of such materials are IPS e.max™ CAD, IPS e.max™ ZirCAD™ Prime, IPS Empress™ CAD and IPS InLine™. All these materials are commercially available products of Ivoclar Vivadent AG, Liechtenstein.

The dental restoration material may as well be a two-component material. In such a material, the two component initiate a redox reaction once they are mixed. Examples of such materials are Variolink™ and Teliolink™. Also these materials are commercially available products of Ivoclar Vivadent AG, Liechtenstein.

The dental restoration material may alternatively be a heat-curing material. Such materials need to be heated for being cured. An example of such a material is SR Ivocap™ which is a commercially available product of Ivoclar Vivadent AG, Liechtenstein. Further examples are Opti-Cryl™ and Veracryl™ which are commercially available products of New Stetic S.A, Columbia.

All of the above materials may be cured in a form. Thereafter, the cured material may be subject to a machining process or a cutting process, e.g. milling, drilling or grinding, in order to reach the desired final form.

In a further example, the dental restoration material is a pre-cured material. Such materials are usually cured in a form. Thereafter, the material may be treated in a subtractive manner, e.g. by machining or cutting. An example of such a material is Tetric™ CAD which is a commercially available product of Ivoclar Vivadent AG, Liechtenstein.

As an alternative to the above materials which are specific dental restoration materials, also plastic materials of different kind may be used. Preferably, the plastic materials are suitable for injection molding and/or 3D printing. Examples of such materials include, but are not limited to polyethylene, polypropylene, polyvinylchloride, polystyrene, polytetrafluoroethylene, polymethylmethacrylate, polyamide, polyester, polycarbonate, polyethylene terephthalate, polyoxymethylene. Also silicones may be used.

As further alternatives to the above materials which are specific dental restoration materials, also inorganic materials of different kind may be used. Preferably, the inorganic materials are machinable by means of milling and/or grinding or can be processed via viscous flow using the hot press technology. Examples of such materials include, but are not limited to silicate glasses and glass-ceramics including lithium silicate glass-ceramics, lithium aluminosilicate glass-ceramics and leucite glass-ceramics as well as oxide ceramics including ZrO2, Al2O3 and feldspar ceramics.

As a fluorescent material of a first type or as a fluorescent material of a second type, phosphors may be used. Phosphors emitting in the green spectrum for example include zinc sulfides which are doped by gold, copper or aluminum, e.g. ZnS:Cu+, ZnS:Au+, ZnS:Al3+. Phosphors emitting in the red spectrum for example include yttrium oxides which may be doped by europium, e.g. Y2O2:Eu3+.

The fluorescent material of the first type or the fluorescent material of the second type may be embedded into a dental restoration material.

At least one of the first sector, the second sector and the third sector, may also comprise pigments. These are non-fluorescent, however, providing pigments is useful when using white light imaging in addition to fluorescence imaging. When known pigments are provided in the calibration unit, color balancing, especially white balancing, can be performed during the calibration. Examples for white pigments include titanium dioxide and zinc oxide.

The problem is additionally solved by a macroscopic medical imaging calibration system, especially a macroscopic dental imaging calibration system. The macroscopic medical imaging calibration system comprises at least one imaging device, at least one calibration unit according to the invention, and at least one excitation device. The at least one excitation device is configured to excite fluorescence of the fluorescent material of the first type. Moreover, the imaging device is configured to capture excitation emissions of the fluorescent material of the first type. A macroscopic medical imaging calibration system is a system for calibrating a macroscopic medical imaging device. Analogously, a macroscopic dental imaging calibration system is a system for calibrating a macroscopic dental imaging device. Again, the term macroscopic is used as a differentiation over microscopic imaging devices or simply microscopes. Using such a macroscopic medical imaging calibration system, especially a macroscopic dental imaging calibration system, the imaging device may be calibrated to a ground truth which is represented by the calibration unit. Thus, if two or more imaging devices are calibrated using the same or similar calibration units, the comparability of the images being produced by these imaging devices is enhanced. This means that images having been captured by one imaging device may be compared with high reliability to images having been captured by another imaging device. Moreover, since the imaging device may be calibrated more than once over time, the comparability of images which have been captured at different points in time is also improved. Moreover, images which have been captured by a calibrated imaging device may be analyzed in a quantitative manner. In the case of a macroscopic dental imaging device, dental pathogens which are represented in the images may be quantified. This enhances a diagnosis being based on the images. Following the above explanations, also the quantitative analyses are made comparable over time and over devices by use of the calibration unit. Altogether, the quality of images being captured by a macroscopic medical imaging device or a macroscopic dental imaging device is improved.

It is noted that the imaging device and the excitation device have been introduced as separate devices. This is just one variant. It is also possible to have the imaging device and the excitation device being formed integrally in one device. Such a device may be called a camera device or a fluorescence imaging system.

It is further noted that the macroscopic medical imaging calibration system according to the invention may also be configured to perform white balancing. In this context, the imaging device is configured to capture a white light image. The sector of the calibration unit comprising the opaque, non-fluorescent material may be used to this end. Alternatively, a white balancing sector may be provided in the calibration unit. Such a white balancing sector may be specifically adapted to perform white balancing.

In a variant, the at least one excitation device may additionally be configured to excite fluorescence of the fluorescent material of the second type. Moreover, the imaging device may be configured to capture excitation emissions of the fluorescent material of the second type.

Thus, also a fluorescence imaging functionality which relates to the fluorescence of the fluorescent material of the second type may be calibrated. Consequently, the quality of fluorescence images is further enhanced.

In a further alternative, two separate excitation devices are provided, wherein one of the excitation devices is configured to excite fluorescence of the fluorescent material of the first type and the other one of the excitation devices is configured to excite fluorescence of the fluorescent material of the second type.

In a case in which the calibration unit comprises a sector with a fluorescent material of a first type and a sector of a fluorescent material of a second type, a method for calibrating the imaging device may comprises exciting the fluorescent material of the first type, capturing excitation emissions of the fluorescent material of the first type, adapting at least one setting of the imaging device, if necessary, and subsequently exciting the fluorescent material of the second type, capturing excitation emissions of the fluorescent material of the second type, and adapting at least one setting of the imaging device, if necessary. In other words, the fluorescent material of the first type and the fluorescent material of the second type are excited subsequently. In the above example, the fluorescent material of the first type is excited before the fluorescent material of the second type. This order can, of course, be inverted. The sequential excitation allows for calibration results of high quality since the emissions from the fluorescent material of the first type and the emissions from the fluorescent material of the second type do not influence each other. In an alternative, the fluorescent material of the first type and the fluorescent material of the second type are excited together. In an alternative of this case, only the emissions of one of these materials are captured in a first step and the emissions of the other material are captured in a second step. Filters may be used to this end. In another alternative, the emissions of both materials are captured simultaneously. Since the fluorescent emissions of the materials are characterized by different wavelengths, one or more filters may be used to separate the emissions from one another. Also these variants allow for a high quality calibration.

In this context, the imaging device may be one of an intra-oral camera, an extra-oral camera and an intra-oral scanner. Such imaging devices are suitable for being used in dental diagnostics.

The problem is further solved by a use of a calibration unit according to the invention for the calibration of a macroscopic medical imaging device, especially for the calibration of a macroscopic dental imaging device. Using such a calibration unit, the macroscopic medical imaging device, especially the macroscopic dental imaging device, may be calibrated to a ground truth, which is represented by the calibration unit. Thus, if two or more macroscopic medical imaging devices or two or more macroscopic dental imaging devices are calibrated using the same or similar calibration units, the comparability of the images being produced by these imaging devices is enhanced. This means that images having been captured by one imaging device may be compared with high reliability to images having been captured by another imaging device. Moreover, since the macroscopic medical imaging device or the macroscopic dental imaging device may be calibrated more than once over time, the use of a calibration unit also enhances the comparability of images which have been captured at different points in time. In other words, using a calibration unit has the effect that captured images are comparable over time and over devices. Moreover, images which have been captured by a calibrated imaging device may be analyzed in a quantitative manner. In the case of a macroscopic dental imaging device, dental pathogens which are represented in the images may be quantified. This enhances a diagnosis being based on the images. Following the above explanations, also the quantitative analyses are made comparable over time and over devices by the use of the calibration unit. Altogether, the quality of images being captured by a macroscopic medical imaging device or a macroscopic dental imaging device is improved.

It is understood that during the use of the calibration unit, ambient light needs to be blocked from influencing the optical interaction of the calibration unit and the imaging device. Blocking the ambient light further improves the calibration quality.

The calibration being performed using the calibration unit may be at least one of a pixel size calibration, a color reception calibration and a color intensity calibration.

BRIEF DESCRIPTION OF THE DRAWINGS

Examples of the invention will be described in the following with reference to the drawings.

DETAILED DESCRIPTION

Figure 1:
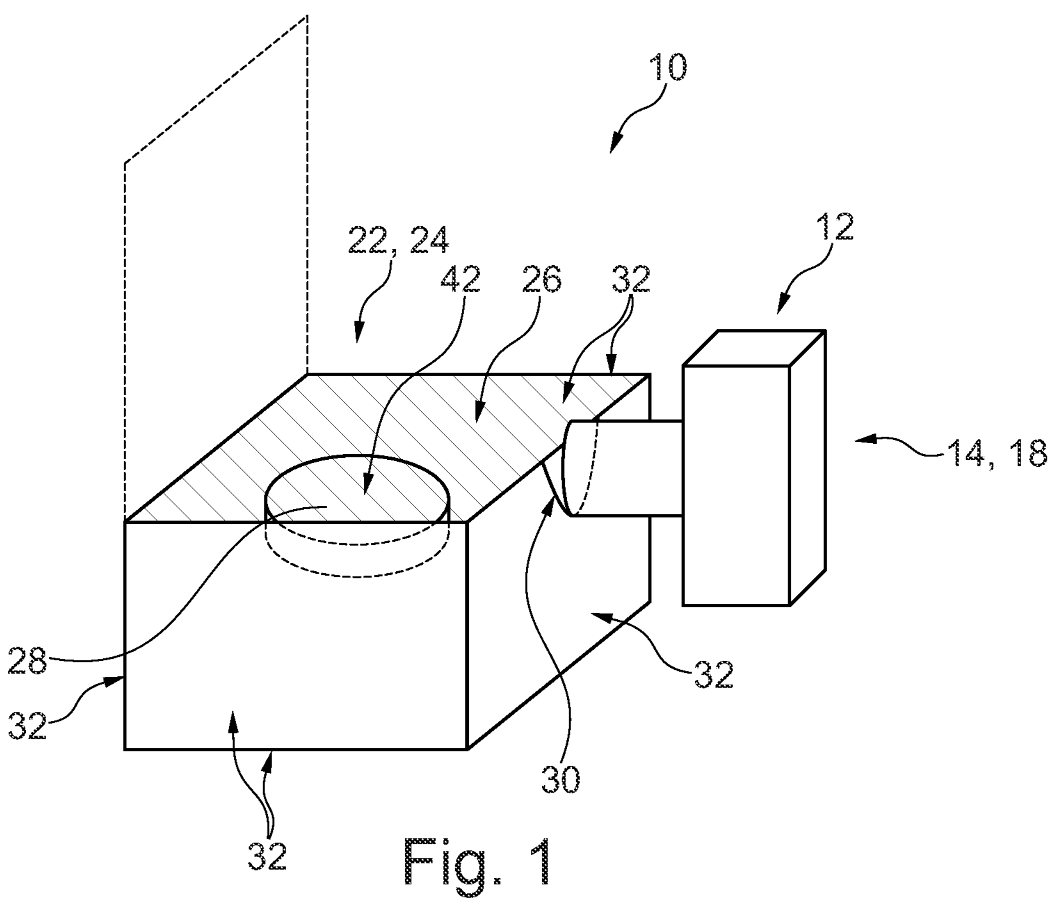
FIG. 1 shows a macroscopic medical imaging calibration system according to the invention which comprises a calibration unit according to the invention.

FIG. 1 shows a macroscopic medical imaging calibration system 10 which is a macroscopic dental imaging calibration system 10 in the examples shown in the Figures. The same reference sign will be used for the macroscopic medical imaging calibration system and the macroscopic dental imaging calibration system.

The macroscopic dental imaging calibration system 10 comprises a camera or camera device 12.

The camera device 12 combines an imager or imaging device 14 having an image capturing optic 16 and an excitation device 18. In the present example, the excitation device comprises a plurality of excitation diodes 20 (cf. FIG. 2).

Figure 2:
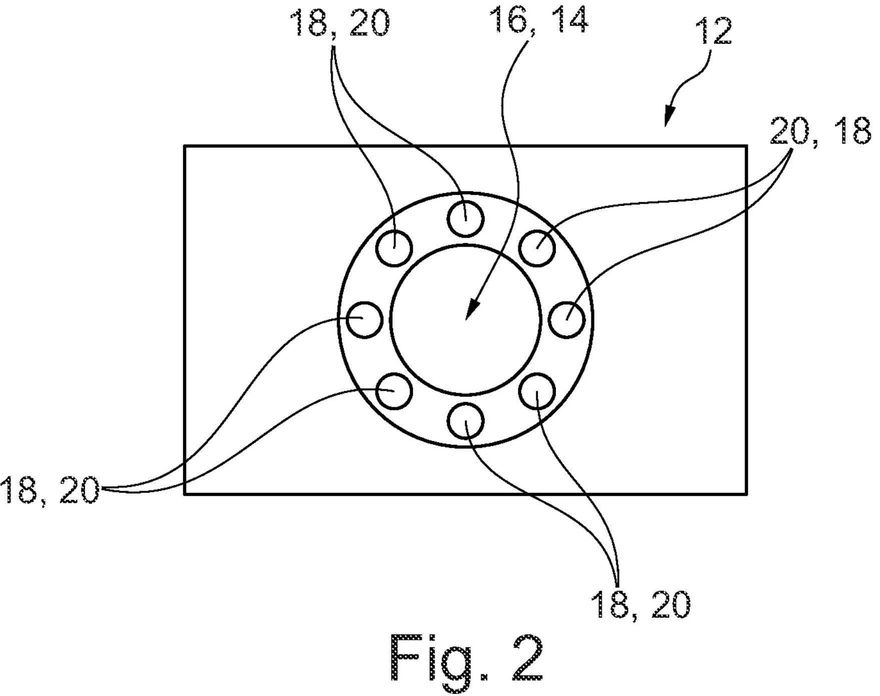
FIG. 2 shows a detail of an imaging device of the macroscopic medical imaging calibration system of FIG. 1.

The camera device 12 as shown in FIGS. 1 and 2 is an extra-oral camera.

The macroscopic dental imaging calibration system 10 also comprises an obscuration device 22 which is realized as an obscuration box 24 in the example of FIG. 1.

The obscuration device 22 has a receptacle 26 for receiving a calibration unit 28 and an opening 30 for receiving a portion of the camera device 12.

Moreover, the obscuration device 22 comprises a number of walls 32 being impervious to light. The walls 32 enclose the receptacle 26 on all sides except for the opening 30. Thus, the obscuration device 22 is able to block ambient light from influencing a calibration of the camera device 12, especially the imaging device 14 using the calibration unit 28.

In the example of FIG. 1, one of the walls 32 which is represented at an upper side of the obscuration device 22 is hinged on an adjacent wall 32 such that it can be selectively opened for arranging the calibration unit 28 in the receptacle 26 and for withdrawing the calibration unit 28 from the receptacle 26.

In FIG. 1, the upper wall is represented as if it were transparent such that the interior of the obscuration device 22 is visible. The upper wall is in a closed state.

Additionally, an open state of the upper wall is represented in dashed lines.

Figure 3:
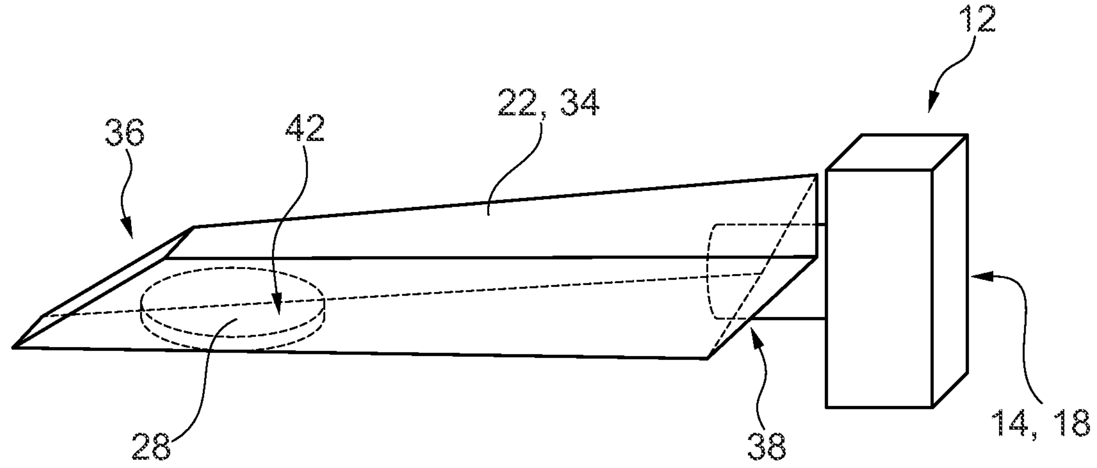
FIG. 3 shows an alternative macroscopic medical imaging calibration system according to the invention which comprises a calibration unit according to the invention.

FIG. 3 shows a variant of the dental imaging calibration system 10.

This variant only differs from the variant as shown in FIG. 1 in that the obscuration device 22 is now formed as an obscuration sleeve 34 made from a flexible material which is impervious to light.

The obscuration sleeve 34 comprises a closed end 36 and an open end 38 which is arranged opposite to the closed end 36.

When in use, the calibration unit 28 is placed in proximity to the closed end 36 in an interior of the obscuration sleeve 34 and a portion of the camera device 12 is received in the open end 38. Thus, also the obscuration sleeve 34 is able to block ambient light from influencing a calibration of the camera device 12, especially the imaging device 14 using the calibration unit 28.

Figure 4:
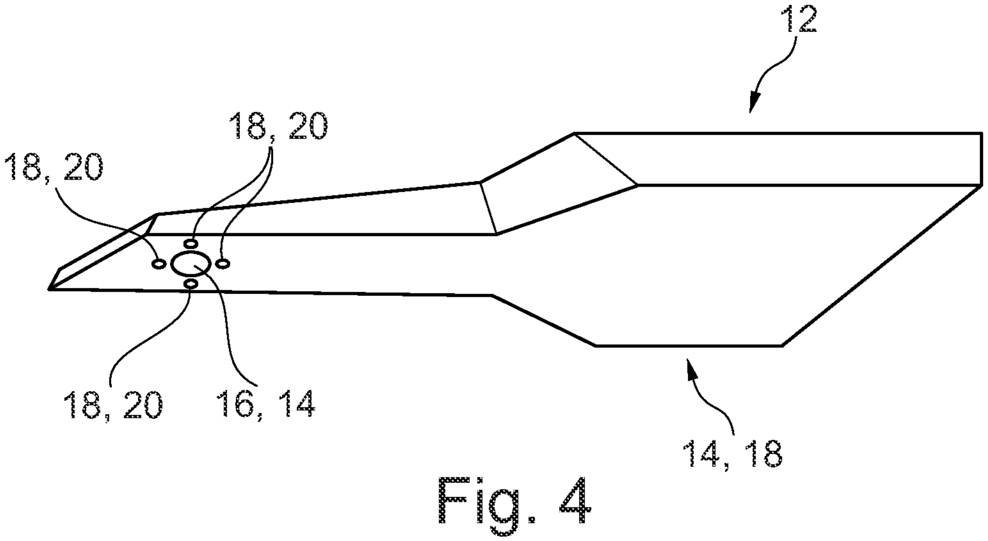
FIG. 4 shows an alternative imaging device which may be used as a replacement of the imaging device as shown in FIGS. 1 to 3.

FIG. 4 shows an alternative camera device 12 which is formed as an intra-oral camera.

Also the camera device 12 of FIG. 4 combines an imaging device 14 having an image capturing optic 16 and an excitation device 18. Again, the excitation device 18 comprises a plurality of excitation diodes 20.

It is understood that the camera device 12 of FIG. 4 may be used instead of the camera device 12 being represented in FIGS. 1 to 3. When using the camera device of FIG. 4, the end of the camera device 12 comprising the image capturing optic 16 and the excitation diodes 20 is arranged inside the obscuration box 24 by putting it through the opening 30 or inside the obscuration sleeve 34 by inserting it through to the open end 38.

The macroscopic dental imaging calibration system 10 of all variants also comprises the calibration unit 28 which is represented in a schematic manner only in FIGS. 1 and 3.

Different embodiments of the calibration unit 28 will be explained in the following with reference to FIGS. 5 to 17.

Figures 5, 6, 7:
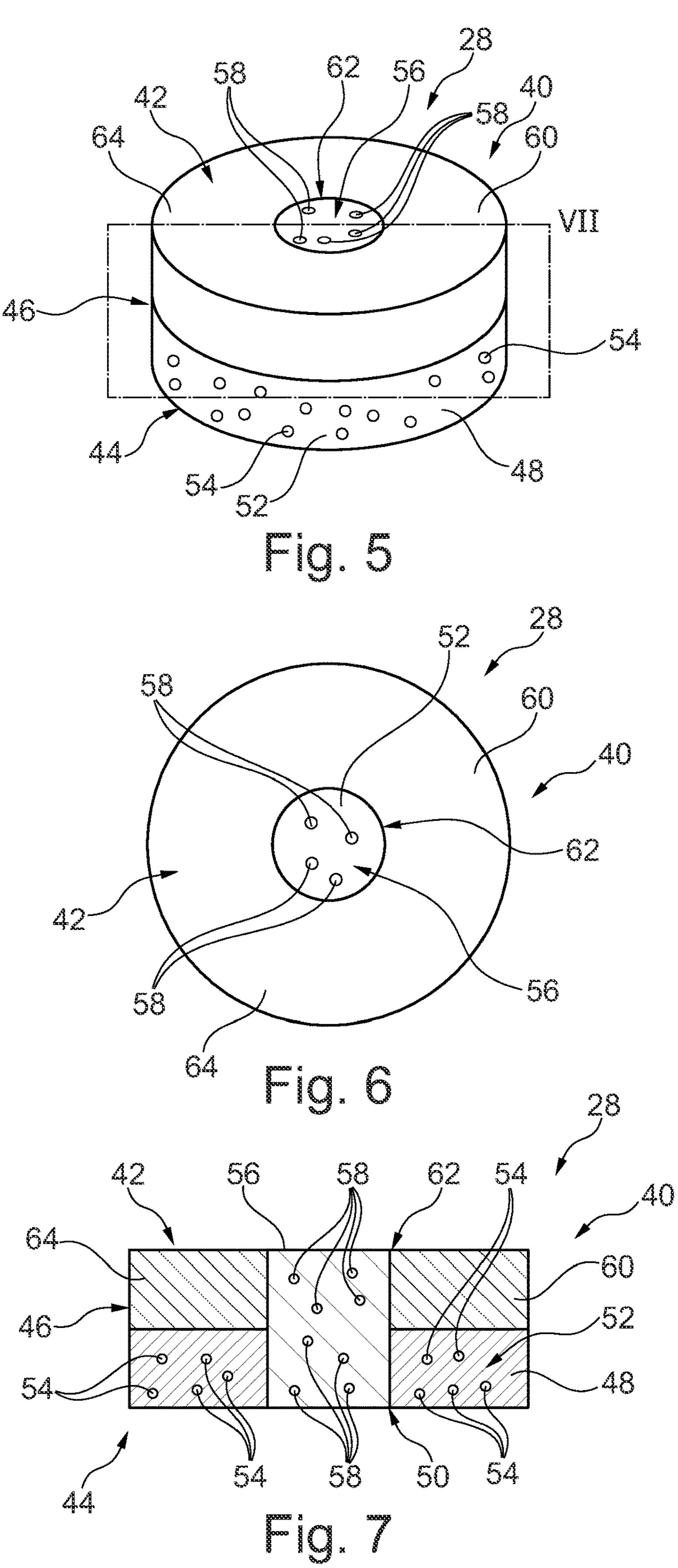
FIG. 5 shows a calibration unit according to a first embodiment of the present invention in a perspective view.
FIG. 6 shows a top view of the calibration unit of FIG. 5.
FIG. 7 shows a sectional view of the calibration unit of FIG. 5 along plane VII.

A first embodiment of the calibration unit 28 is shown in FIGS. 5 to 7.

In this embodiment, the calibration unit 28 comprising a main body 40 which is generally shaped as a circular disk.

The main body 40 has a front surface 42 being an upper surface in the representation of FIG. 5 and a back surface 44 being a lower surface in the representation of FIG. 5.

Between the front surface 42 and the back surface 44 a lateral surface 46 spans which has the form of a tube with a circular cross section.

The front surface 42 is configured for being optically oriented towards the imaging device 14, i.e. the camera device 12 (see also FIGS. 1 and 3).

The calibration unit 28 comprises a first sector 48.

In the present embodiment, the first sector is formed as a layer of the main body 40.

The layer is ring shaped and has an opening 50 at its center.

The first sector 48 extends parallel to the front surface 42 and parallel to the back surface 44.

At the same time, the back surface 44 of the main body 40 is formed by a lower side of the first sector 48, i.e. the first sector 48 is arranged at a lower end of the main body 40.

A thickness of the first sector 48 being formed as an annular layer covers substantially half the thickness of the disk-shaped main body 40. Thus, the first sector 48 is arranged at a distance from the front surface 42.

In the present example, the first sector 48 is made from a dental restoration material 52 into which particles of a fluorescent material 54 of a first type are embedded. For better visibility, only some particles of fluorescent material 54 of the first type are provided with a reference sign.

The dental restoration material is a material which is able to replace dentin.

The fluorescent material 54 of the first type is a green fluorescent material.

The calibration unit 28 also comprises a second sector 56.

The second sector 56 has the form of a circular cylinder. A diameter of the circular cylinder corresponds to a diameter of the opening 50 and the circular cylinder forming the second sector 56 is arranged inside the opening 50 such that a lower surface of the second sector 56 coincides with the back surface 44.

Moreover, an upper end face of the circular cylinder forming the second sector 56 coincides with the front surface 42.

Thus, the second sector 56 spans between the back surface 44 and the front surface 42. In other words, a height of the circular cylinder forming the second sector 56 corresponds to a thickness of the main body 40.

In the present example, the second sector 56 is made from the dental restoration material 52 into which particles of a fluorescent material 58 of a second type are embedded. For better visibility, only some particles of fluorescent material 58 of the second type are provided with a reference sign.

The fluorescent material 58 of the second type is a red fluorescent material.

Thus, the fluorescent material 58 of the second type is different from the fluorescent material 54 of the first type.

Moreover, the calibration unit 28 comprises a fourth sector 60.

It is noted that the designation of the sectors as first, second and fourth is done for the ease of explanation only. No specific number of sectors is implied.

Also the fourth sector 60 is formed as a layer of the main body 40.

The layer is ring shaped and has an opening 62 at its center.

The first sector 48 and the fourth sector 60 are arranged in a congruent manner.

This means that an external diameter of the first sector 48 and the fourth sector 60 is the same. Also a diameter of the opening 50 and the opening 62 are the same.

The fourth sector 60 extends parallel to the front surface 42 and parallel to the back surface 44.

At the same time, the front surface 42 of the main body 40 is formed by an upper side of the fourth sector 60. A lower side of the fourth sector 60 coincides with an upper side of the first sector 48.

Thus, also a thickness of the fourth sector 60 being formed as an annular layer covers substantially half the thickness of the disk-shaped main body 40.

The second sector 56 extends through the opening 62. In other words, the fourth sector 60 partially surrounds the second sector 56.

In the present example, the fourth sector is made from a translucent material 64, especially a transparent material.

It is noted that the first sector 48, the second sector 56 and the fourth sector 60 are separate from one another.

In the calibration unit 28 according to the first embodiment, the first sector 48 mimics sound teeth. The second sector 56 mimics a carious lesion and the fourth sector 60 mimics enamel.

Using such a calibration unit 28, an imaging device 14 may be calibrated in a highly reliable manner.

Figures 8, 9, 10:
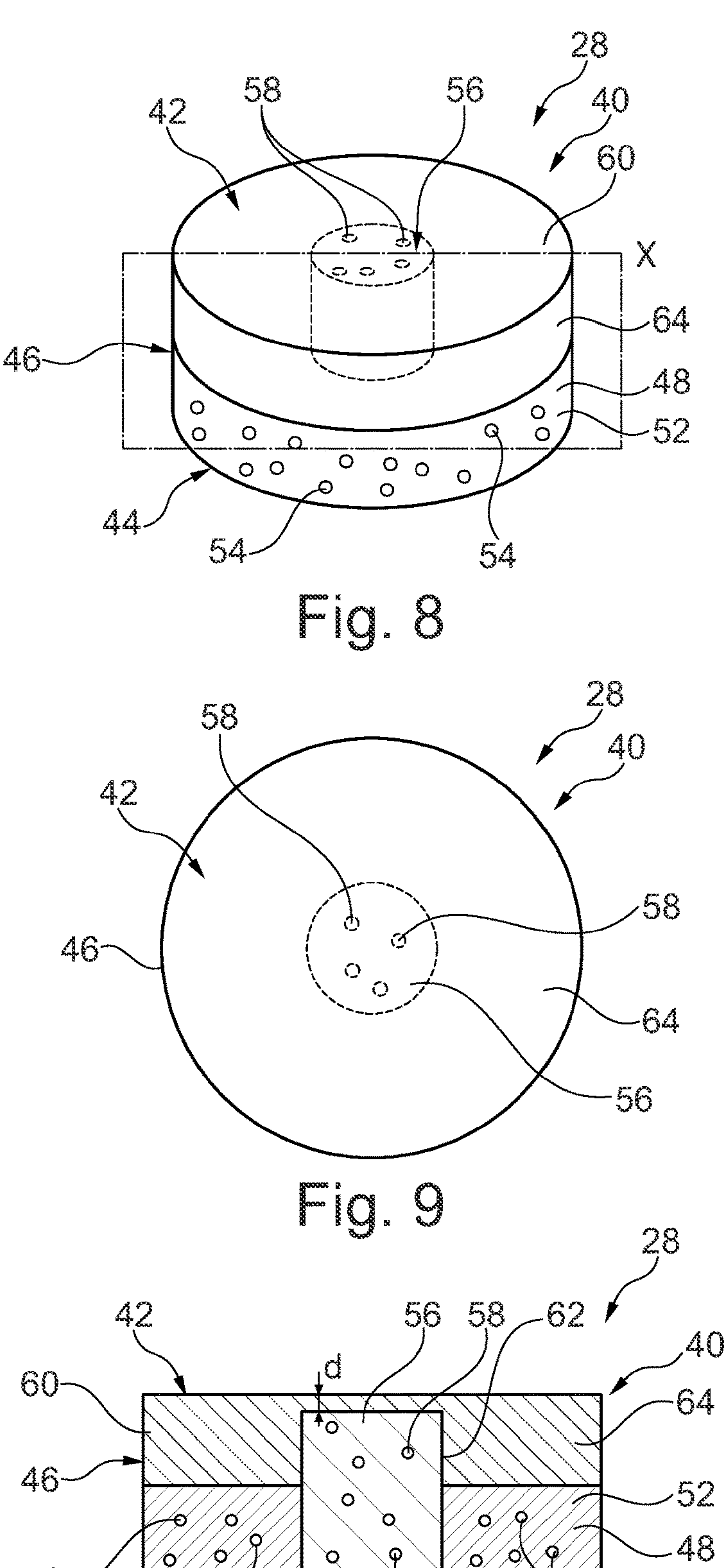
FIG. 8 shows a calibration unit according to a second embodiment of the present invention in a perspective view.
FIG. 9 shows a top view of the calibration unit of FIG. 8.
FIG. 10 shows a sectional view of the calibration unit of FIG. 8 along plane X.

A second embodiment of the calibration unit 28 is shown in FIGS. 8 to 10.

In the following, only the differences with respect to the first embodiment are explained. Same or corresponding elements are designated with the same reference signs.

The second embodiment differs from the first embodiment in that an upper end surface of the second sector 56 is arranged at a distance d from the front surface 42. Thus, a height of the second sector 56 being cylinder-shaped is shorter than a thickness of the main body 40.

The space between the upper end surface of the second sector 56 and the front surface 42 now forms part of the fourth sector 60 and is filled with translucent, more specifically transparent, material 64. In other words, the opening 62 now is a blind hole.

For that reason, the second sector 56 is visible in FIGS. 8 and 9 even though it is covered by a portion of the fourth sector 60.

In the calibration unit 28 according to the second embodiment, the first sector 48 again mimics sound teeth and the fourth sector 60 mimics enamel.

The second sector 56 now mimics a sub-surface carious lesion. Such a lesion is covered by enamel.

Also using the calibration unit 28 of the second embodiment, an imaging device 14 may be calibrated in a highly reliable manner.

Figure 11:
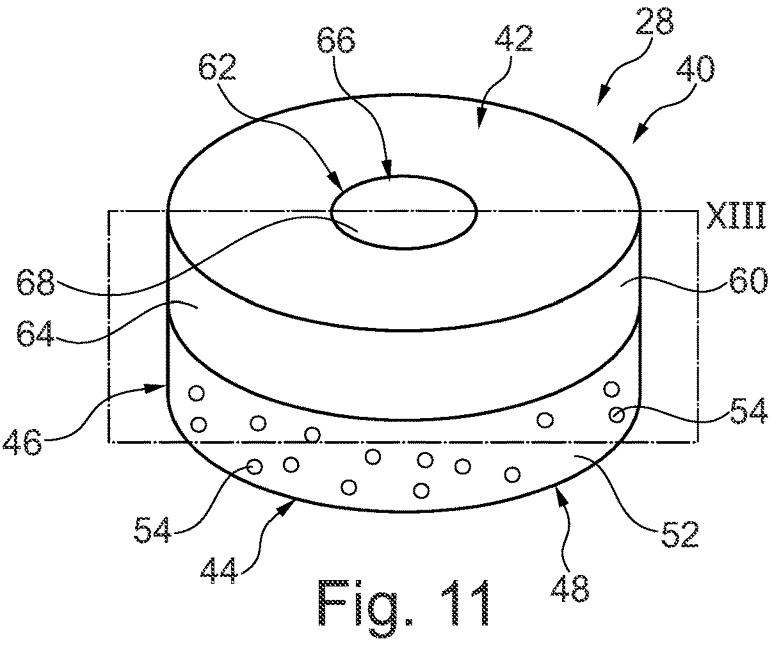
FIG. 11 shows a calibration unit according to a third embodiment of the present invention in a perspective view.
Figure 12:
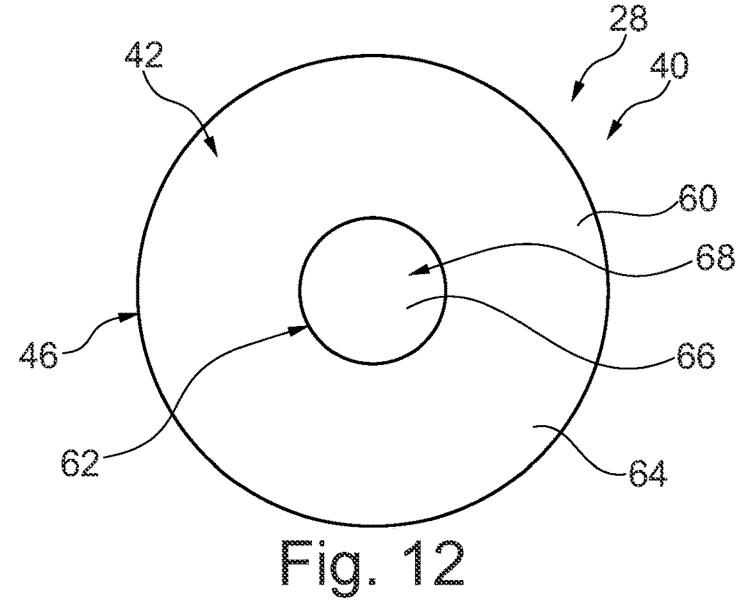
FIG. 12 shows a top view of the calibration unit of FIG. 11.
Figure 13:
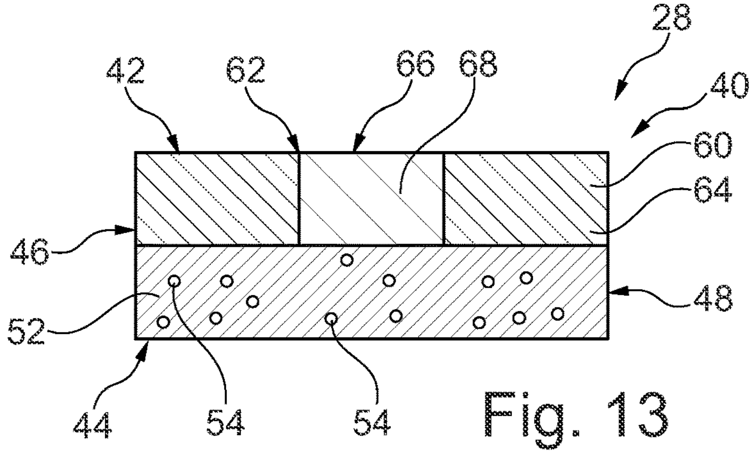
FIG. 13 shows a sectional view of the calibration unit of FIG. 11 along plane XIII.
Figure 14:
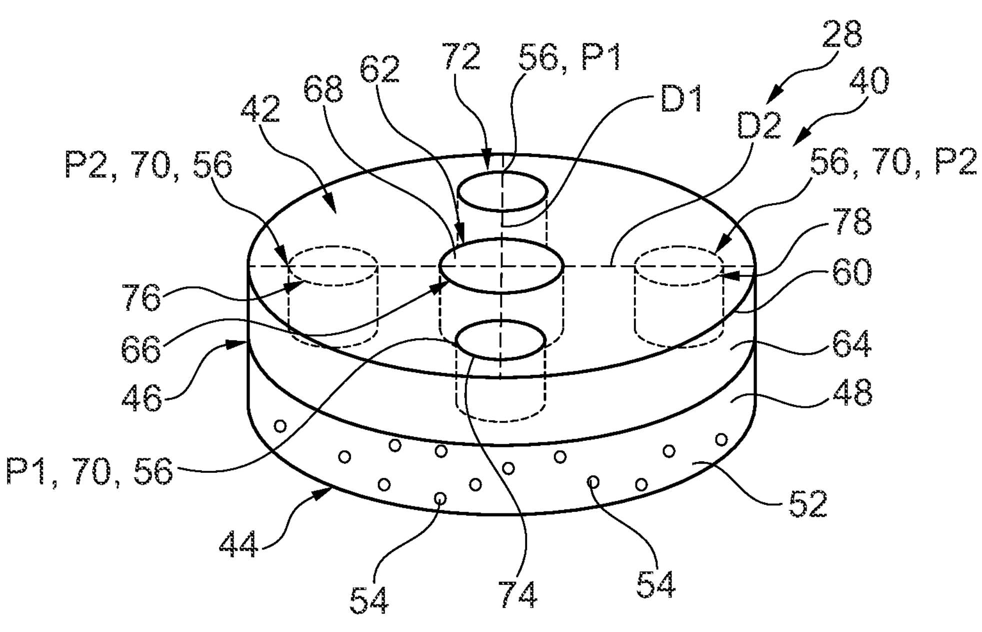
FIG. 14 shows a calibration unit according to a fourth embodiment of the present invention in a perspective view.
Figure 15:
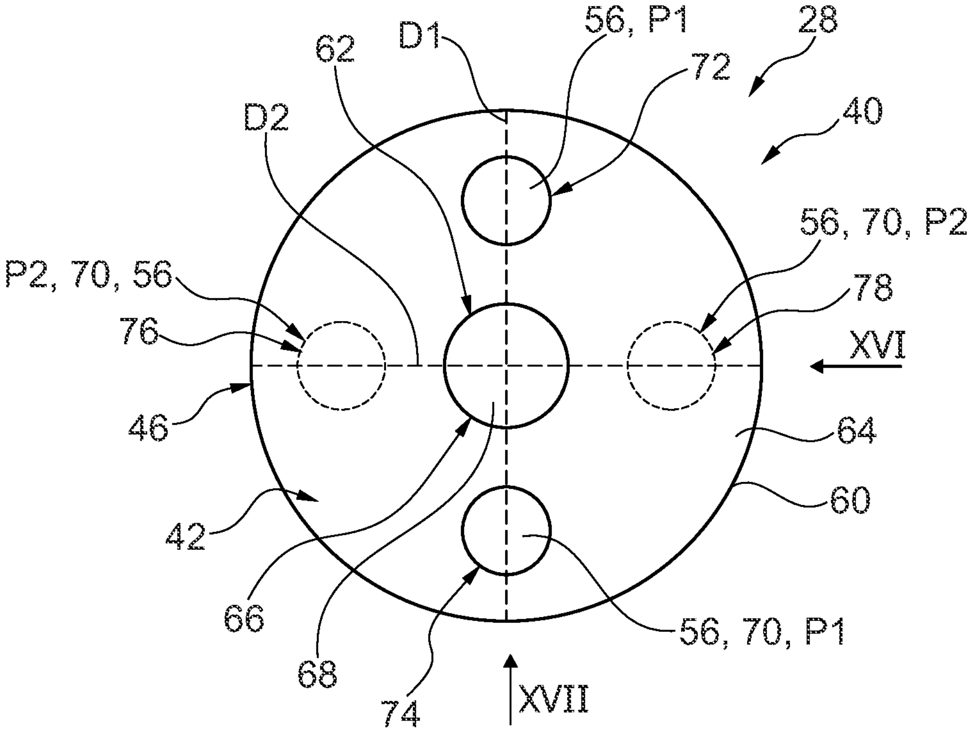
FIG. 15 shows a top view of the calibration unit of FIG. 14.
Figure 16:
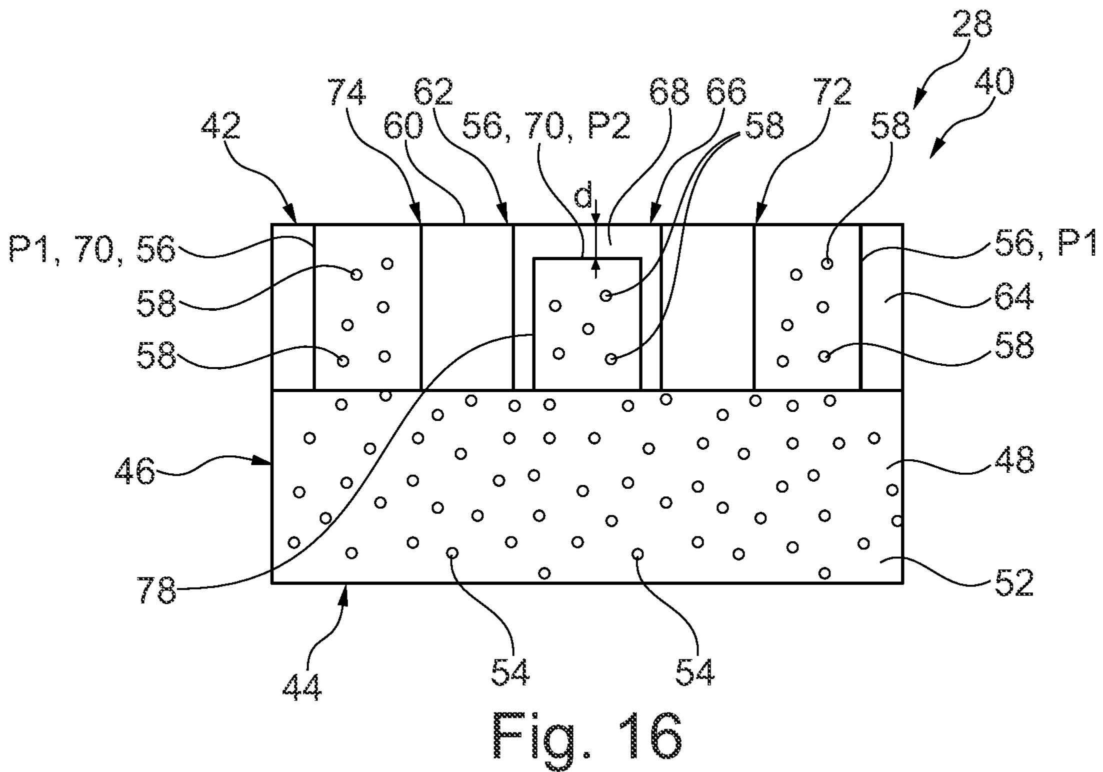
FIG. 16 shows a side view of the calibration unit of FIG. 14 along direction XVI.
Figure 17:
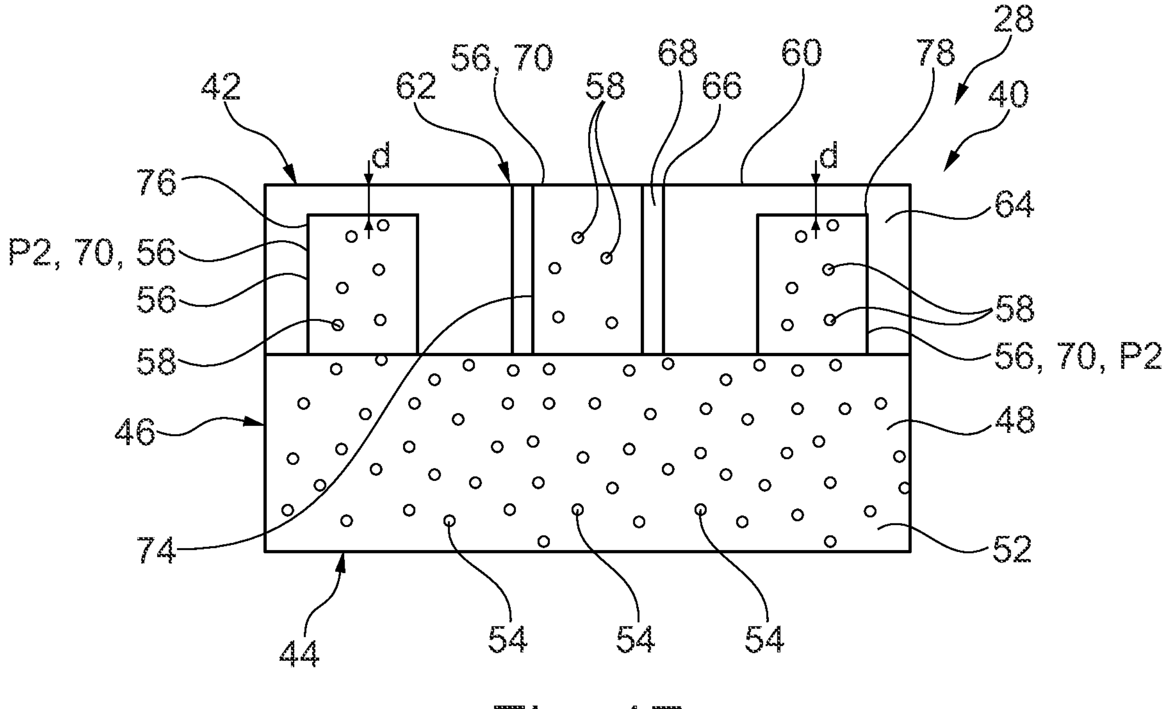
FIG. 17 shows a side view of the calibration unit of FIG. 14 along direction XVII.

A third embodiment of the calibration unit 28 is shown in FIGS. 11 to 13.

Again, only the differences with respect to the first embodiment and the second embodiment are explained. Same or corresponding elements are designated with the same reference signs.

As compared to the first and second embodiments, the first sector 48 now is disk-shaped, i.e. the first sector 48 does not comprise an opening 50.

The fourth sector 60 corresponds to the fourth sector 60 of the first embodiment.

However, instead of a second sector 56, a third sector 66 is provided.

The third sector 66 is cylinder-shaped and is arranged in the opening 62 of the fourth sector 60.

The third sector 66 fills the opening 62 completely.

An upper end surface of the third sector 66 coincides with the front surface 42. A lower end surface of the third sector 66 coincides with a lower end surface of the fourth sector 60.

In the present example, the third sector 66 is made from an opaque, non-fluorescent material 68.

It is noted that the third sector 66 is separate from the first sector 48 and the fourth sector 60.

In the calibration unit 28 according to the third embodiment, the first sector 48 mimics sound teeth. The third sector 66 mimics a white-spot lesion and the fourth sector 60 mimics enamel.

Using such a calibration unit 28, an imaging device 14 may be calibrated in a highly reliable manner.

A fourth embodiment of the calibration unit 28 is shown in FIGS. 14 to 17.

As before, only the differences with respect to the previous embodiments are explained. Same or corresponding elements are designated with the same reference signs.

The calibration unit 28 according to the fourth embodiment comprises a first sector 48 which corresponds to the first sector of the third embodiment of the calibration unit, i.e. the first sector 48 of the fourth embodiment of the calibration unit 28 is disk-shaped without an opening.

Moreover, the calibration unit 28 according to the fourth embodiment comprises a third sector 66 which corresponds to the third sector 66 of the third embodiment. Thus, the third sector 66 is cylinder-shaped and is arranged centrally within the calibration unit 28.

Additionally, the calibration unit 28 according to the fourth embodiment comprises a total of four second sectors 56.

A first pair P1 of second sectors 56 is arranged on a first diameter D1 of the calibration unit 28, wherein one second sector 56 forming part of the first pair P1 is arranged on a first side of the third sector 66 between the third sector 66 and the lateral surface 46. The other second sector 56 forming part of the first pair P1 is arranged on an opposite side of the third sector 66 between the third sector 66 and the lateral surface 46.

The second sectors 56 of the first pair P1 have the form of a circular cylinder, respectively.

An upper end surface of the second sectors 56 of the first pair P1 coincides with the front surface 42. A lower end surface of the second sectors 56 of the first pair P1 coincides with an upper end face of the first sector 48.

A second pair P2 of second sectors 56 is arranged on a second diameter D2 of the calibration unit 28.

The second diameter D2 extends substantially perpendicular to the first diameter D1.

One second sector 56 forming part of the second pair P2 is arranged on a first side of the third sector 66 between the third sector 66 and the lateral surface 46. The other second sector 56 forming part of the second pair P2 is arranged on an opposite side of the third sector 66 between the third sector 66 and the lateral surface 46.

The second sectors 56 of the second pair P2 have the form of a circular cylinder, respectively.

An upper end surface of the second sectors 56 of the second pair P2 is arranged at a distance d from the front surface 42 (cf. second embodiment of the calibration unit 28). A lower end surface of the second sectors 56 of the first pair coincides with an upper end face of the first sector 48.

A diameter of all second sectors 56 is substantially the same.

When comparing the fourth embodiment of the calibration unit 28 to the first and second embodiment of the calibration unit, the calibration unit 28 of the fourth embodiment comprises three more second sectors 56. For that reason, the second to fourth second sectors 56 can also be called supplementary sectors 70.

The calibration unit 28 of the fourth embodiment also comprises a fourth sector 60. The fourth sector 60 is formed as a layer as in the previous embodiments.

In the fourth embodiment, the fourth sector 60 comprises five openings, wherein the central opening 62 receives the third sector 66 as in the third embodiment.

The remaining openings 72, 74, 76, 78 receive one of the second sectors 56, respectively.

In this context, the openings 72, 74 receive the second sectors 56 of the first pair P1, respectively. These openings are formed as through holes.

The openings 76, 78 receive the second sectors 56 of the second pair P2, respectively. These openings are formed as blind holes.

In the calibration unit 28 according to the fourth embodiment, the first sector 48 mimics sound teeth. The third sector 66 mimics a white-spot lesion and the fourth sector 60 mimics enamel.

The second sectors 56 of the first pair P1 mimic a carious lesion on a surface and the second sectors 56 of the second pair P2 mimic a sub-surface carious lesion.

Using such a calibration unit 28, an imaging device 14 may be calibrated in a highly reliable manner. Due to the supplementary sectors 70, the calibration is particularly uniform over a field of view of the imaging device 14.

The calibration unit 28 of all of the above embodiments can be used for calibrating the camera device 12, more particularly the imaging device 14.

To this end, the excitation device 18 is configured to excite fluorescence of the fluorescent material 54 of the first type and of the fluorescent material 58 of the second type.

Moreover, the imaging device 14 is configured to capture excitation emissions of the fluorescent material 54 of the first type and of the fluorescent material 58 of the second type.

When using the calibration unit 28 according to the first, second and fourth embodiment for calibrating the camera device 12, using the excitation device 18, both the fluorescent material 54 of the first type and the fluorescent material 58 of the second type are excited.

In a first step, only the excitation emissions of the fluorescent material 54 of the first type may be captured using the imaging device 14.

In a second step, only the excitation emissions of the fluorescent material 58 of the second type may be captured using the imaging device 14.

In order to capture only excitation emissions of one of the fluorescent materials 54, 58 filters may be used.

The calibration being performed using the calibration unit 28 may be at least one of a pixel size calibration, a color reception calibration and a color intensity calibration.

REFERENCE SIGNS

- 10 macroscopic medical imaging calibration system, macroscopic dental imaging calibration system
- 12 camera device
- 14 imaging device
- 16 image capturing optic
- 18 excitation device
- 20 excitation diode
- 22 obscuration device
- 24 obscuration box
- 26 receptacle
- 28 calibration unit
- 30 opening
- 32 wall
- 34 obscuration sleeve
- 36 closed end of the obscuration sleeve
- 38 open end of the obscuration sleeve
- 40 main body of the calibration unit
- 42 front surface
- 44 back surface
- 46 lateral surface
- 48 first sector
- 50 opening
- 52 dental restoration material
- 54 fluorescent material of a first type
- 56 second sector
- 58 fluorescent material of a second type
- 60 fourth sector
- 62 opening
- 64 translucent material
- 66 third sector
- 68 opaque, non-fluorescent material
- 70 supplementary sector
- 72 opening
- 74 opening
- 76 opening
- 78 opening d distance
D1 first diameter
D2 second diameter
P1 first pair
P2 second pair

The invention claimed is:

1. A calibration unit (28) for the calibration of a macroscopic medical imaging device (14), comprising a generally disk-shaped main body (40) having a front surface (42) being configured for being optically oriented towards the imaging device (14), wherein a fluorescent material (54) of a first type is arranged in a first sector (48) of the main body (40), the first sector (48) being a volumetric portion of the main body (40) and formed as a layer of the disk-shaped main body, and a. wherein a fluorescent material (58) of a second type is arranged in a second sector (56) of the main body (40), the second sector (56) being a volumetric portion of the main body (40), the first sector (48) and the second sector (56) being separate from one another and the fluorescent material (54) of the first type being different from the fluorescent material (58) of the second type and/or b. wherein an opaque, non-fluorescent material (68) is arranged in a third sector (66) of the main body (40), the third sector (66) being a volumetric portion of the main body (40), and the third sector (66) being separate from each of the first sector (48) and the second sector (56), and wherein a translucent material (64) is arranged in a fourth sector (60) of the main body (40), the fourth sector (60) being a volumetric portion of the main body (40), and the fourth sector (60) being separate from each of the first sector (48), the second sector (56), and the third sector (66), wherein the fourth sector (60) is formed as a layer of the disk-shaped main body and wherein the second sector (56) and/or the third sector (55) is fully or partially embedded in the fourth sector.

2. The calibration unit (28) according to claim 1, wherein at least one of the first sector (48), the second sector (56) and the third sector (66) is at least partially surrounded by the fourth sector (60).

3. The calibration unit (28) according to claim 1, wherein the main body (40) comprises at least one supplementary sector (70), the supplementary sector (70) being a volumetric portion of the main body (40) and being separate from each of the first sector (48), the second sector (56), and the third sector (66), wherein the fluorescent material (54) of the first type, the fluorescent material (58) of the second type or the opaque, non-fluorescent material (68) is arranged in the supplementary sector (70).

4. The calibration unit (28) according to claim 1, wherein at least one of the first sector (48), the second sector (56), the third sector (66), the fourth sector (60), and the supplementary sector (70) is formed as a layer of the main body (40), wherein the layer extends parallel to the front surface (42).

5. The calibration unit (28) according to claim 4, wherein the layer is arranged at a distance from the front surface (42).

6. The calibration unit (28) according to claim 1, wherein at least one of the first sector (48), the second sector (56), the third sector (66), and the supplementary sector (70) is cylinder-shaped, cone-shaped, polyhedron-shaped or ellipsoid-shaped.

7. The calibration unit (28) according to claim 6, wherein the front surface (42) coincides with an end surface of at least one of the first sector (48), the second sector (56), the third sector (66), and the supplementary sector (70).

8. The calibration unit (28) according to claim 6, wherein an end face being oriented towards the front surface (42) of at least one of the first sector (48), the second sector (56), the third sector (66), and the supplementary sector (70) is arranged at a distance (d) from the front surface (42).

9. The calibration unit (28) according to claim 1, wherein the fluorescent material (54) of the first type is a green fluorescent material.

10. The calibration unit (28) according to claim 1, wherein the fluorescent material (58) of the second type is a red fluorescent material.

11. The calibration unit (28) according to claim 1, wherein at least one of the first sector (48), the second sector (56), the third sector (66), the fourth sector (60) and the supplementary sector (70) comprises a dental restoration material (52).

12. A macroscopic medical imaging calibration system (10), comprising at least one imaging device (14), at least one calibration unit (28) according to claim 1, and at least one excitation device (18), wherein the at least one excitation device (18) is configured to excite fluorescence of the fluorescent material (54) of the first type, and wherein the imaging device (14) is configured to capture excitation emissions of the fluorescent material (54) of the first type.

13. The macroscopic medical imaging calibration device (10) according to claim 12, wherein the imaging device (14) is one of an intra-oral camera, an extra-oral camera and an intra-oral scanner.

14. A method of using the calibration unit (28) according to claim 1 for the calibration of a macroscopic medical imaging device (14), comprising calibrating the macroscopic medical imaging device (14).

15. The calibration unit (28) according to claim 1, wherein the macroscopic medical imaging device (14) is a macroscopic dental imaging device (14).

16. The macroscopic medical imaging calibration system (10) according to claim 12, wherein the macroscopic medical imaging calibration system (10) is a macroscopic dental imaging calibration system (10).

17. The method according to claim 14, wherein the macroscopic medical imaging device (14) is a macroscopic dental imaging device (14).

* * * * *